United States Patent [19]
Hayhurst

[11] Patent Number: 5,647,874
[45] Date of Patent: Jul. 15, 1997

[54] ANCHORING AND MANIPULATING TISSUE

[75] Inventor: John O. Hayhurst, 14751 SE. Wanda Dr., Milwaukie, Oreg. 97267

[73] Assignee: John O. Hayhurst, Portland, Oreg.

[21] Appl. No.: 487,009

[22] Filed: Jun. 7, 1995

Related U.S. Application Data

[60] Continuation of Ser. No. 715,113, Jun. 12, 1991, Pat. No. 5,601,557, which is a division of Ser. No. 192,813, Apr. 20, 1988, abandoned, which is a continuation-in-part of Ser. No. 848,341, Apr. 4, 1986, Pat. No. 4,741,330, which is a continuation of Ser. No. 496,116, May 19, 1983, abandoned, which is a continuation-in-part of Ser. No. 380,043, May 20, 1982, abandoned.

[51] Int. Cl.$^6$ ..................................................... A61B 17/56
[52] U.S. Cl. .............................................. 606/72; 606/232
[58] Field of Search ................................ 606/72, 73, 224, 606/225, 232, 233, 226, 228

[56] References Cited

U.S. PATENT DOCUMENTS

| | | | |
|---|---|---|---|
| 2,065,659 | 12/1936 | Cullen . | |
| 2,562,419 | 4/1951 | Ferris . | |
| 2,669,774 | 1/1954 | Livingston . | |
| 2,883,096 | 4/1959 | Dawson . | |
| 3,103,666 | 9/1963 | Bone . | |
| 3,123,077 | 3/1964 | Alcamo . | |
| 3,399,432 | 9/1968 | Mercer . | |
| 3,470,834 | 10/1969 | Bone . | |
| 3,527,233 | 9/1970 | Shein . | |
| 3,570,447 | 3/1971 | Lemole . | |
| 3,695,271 | 10/1972 | Chodorow . | |
| 3,699,969 | 10/1972 | Allen . | |
| 3,716,058 | 2/1973 | Tanner . | |
| 3,845,772 | 11/1974 | Smith | 606/232 |
| 3,875,648 | 4/1975 | Bone . | |
| 3,910,281 | 10/1975 | Kletschka . | |
| 3,931,667 | 1/1976 | Mercer . | |
| 3,976,079 | 8/1976 | Samuels | 606/232 |
| 3,990,619 | 11/1976 | Russell . | |
| 4,006,747 | 2/1977 | Kronenthal . | |
| 4,013,071 | 3/1977 | Rosenberg . | |
| 4,185,636 | 1/1980 | Gobbax . | |
| 4,235,238 | 11/1980 | Ogiu . | |
| 4,275,490 | 6/1981 | Bivins | 606/72 |
| 4,275,717 | 6/1981 | Bolesky . | |
| 4,287,807 | 9/1981 | Pacharis . | |
| 4,291,698 | 9/1981 | Fuchs . | |
| 4,326,531 | 4/1982 | Shimonaka . | |
| 4,409,974 | 10/1983 | Freeland | 606/232 |
| 4,454,875 | 6/1984 | Pratt . | |
| 4,462,395 | 7/1984 | Johnson . | |
| 4,469,101 | 9/1984 | Coleman . | |
| 4,493,323 | 1/1985 | Albright . | |
| 4,590,928 | 5/1986 | Hunt . | |
| 4,602,635 | 7/1986 | Mulhollan . | |
| 4,621,640 | 11/1986 | Mulhollan . | |
| 4,632,100 | 12/1986 | Somers . | |
| 4,667,675 | 5/1987 | Davis . | |
| 4,669,473 | 6/1987 | Richards . | |
| 4,708,132 | 11/1987 | Silvestrini . | |
| 4,738,255 | 4/1988 | Goble . | |
| 4,776,328 | 10/1988 | Frey . | |

FOREIGN PATENT DOCUMENTS

| | | |
|---|---|---|
| 0129442 | 6/1984 | European Pat. Off. . |
| 0129422 | 12/1984 | European Pat. Off. . |
| 0241240 | 10/1987 | European Pat. Off. . |
| 88904139 | 11/1991 | European Pat. Off. . |
| 2118474 | 11/1983 | United Kingdom . |
| 86/03666 | 7/1986 | WIPO . |
| 87/01270 | 3/1987 | WIPO . |

*Primary Examiner*—Michael A. Brown
*Attorney, Agent, or Firm*—Klarquist Sparkman Campbell Leigh & Whinston, LLP

[57] ABSTRACT

A method whereby an anchor member is configured to provide anchorage of its attached suture within a hole drilled in a bone.

7 Claims, 3 Drawing Sheets

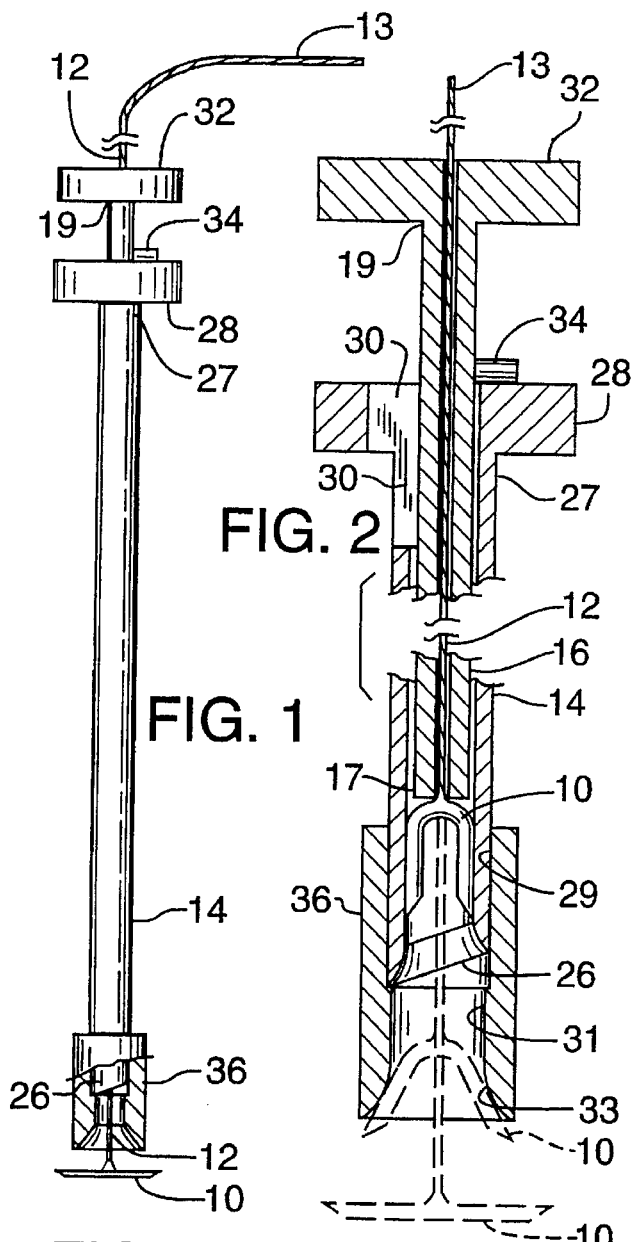
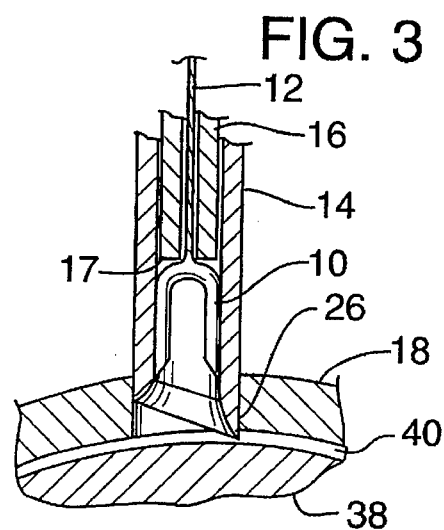
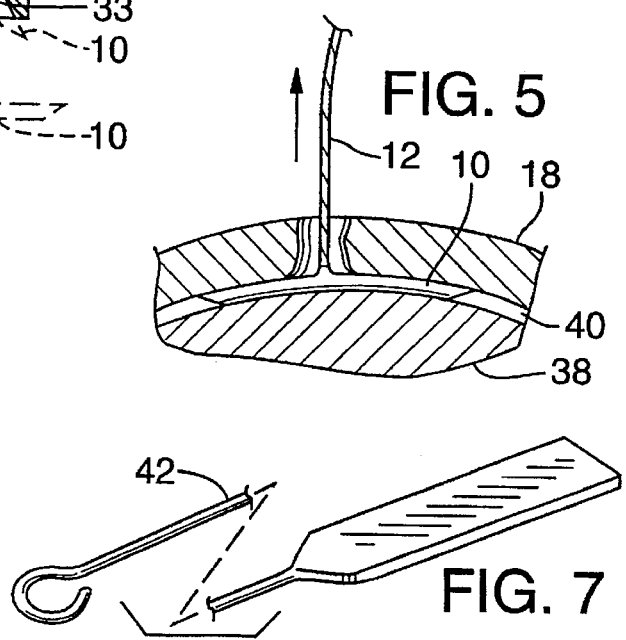

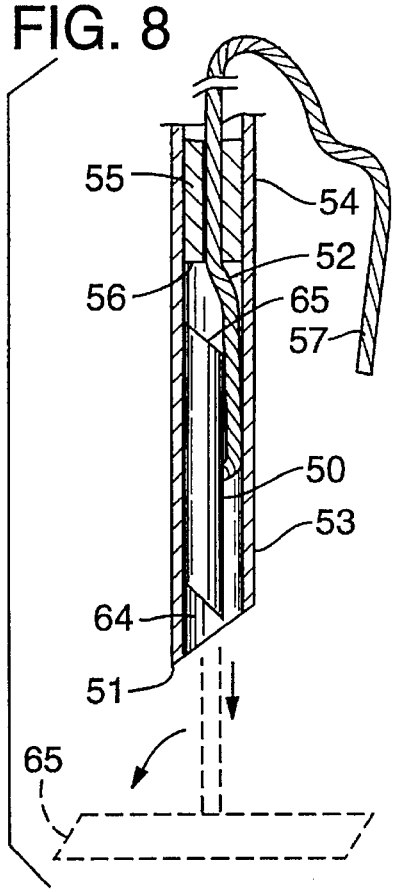
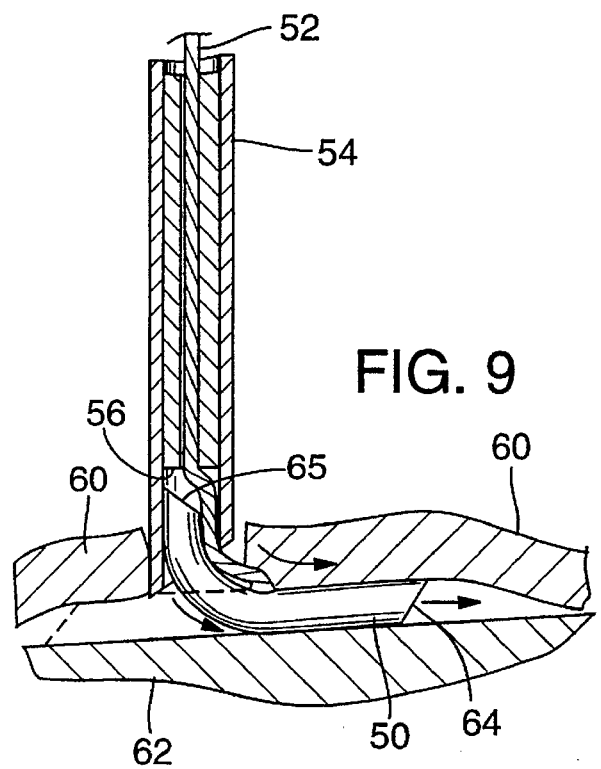
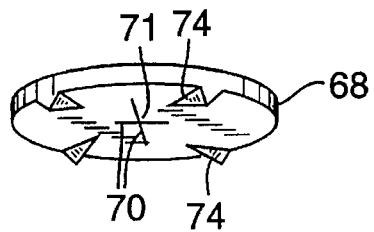
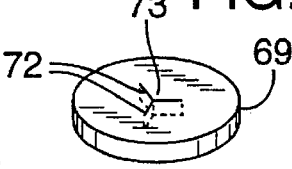
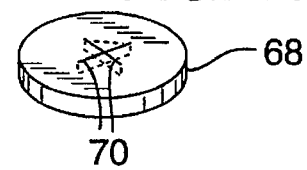
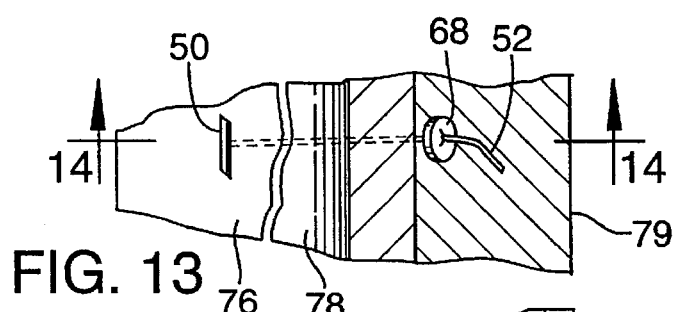
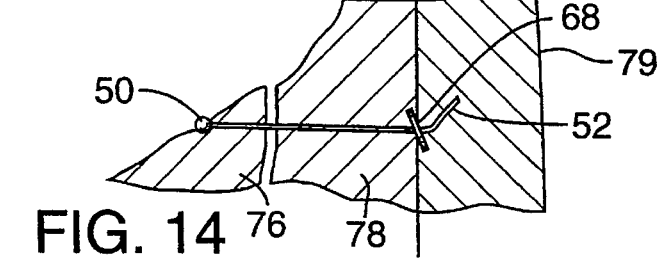

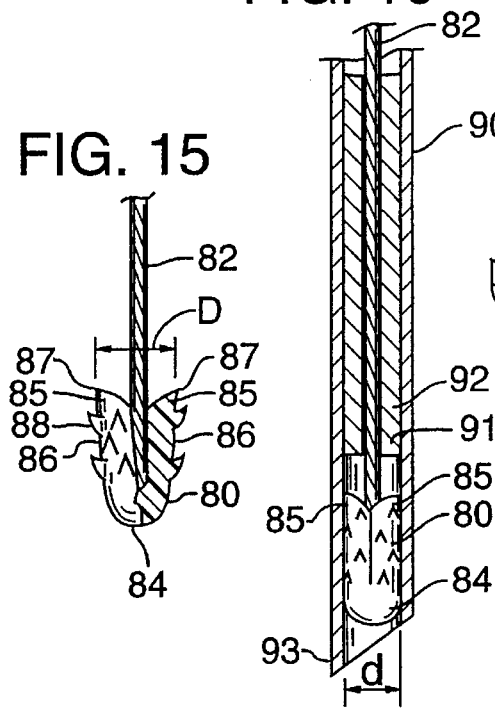
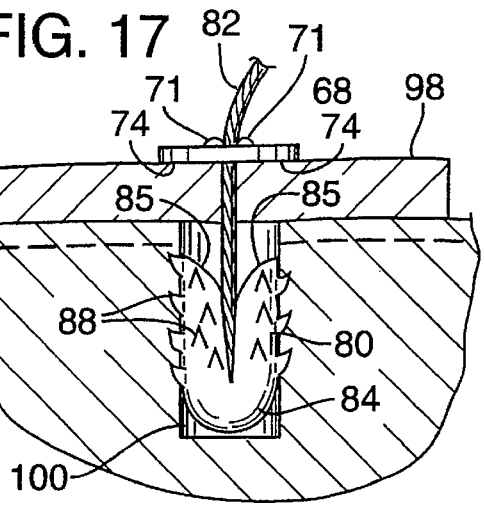
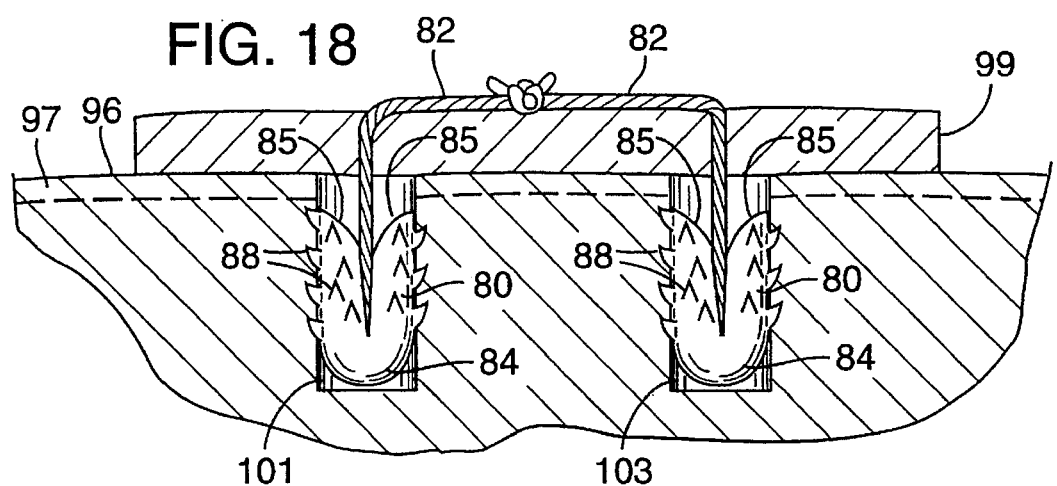
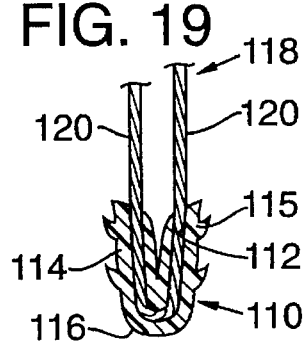
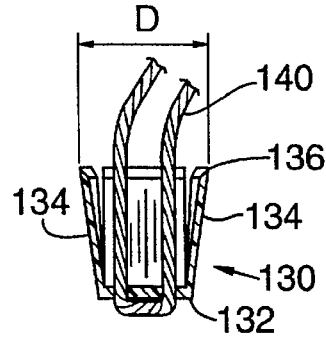
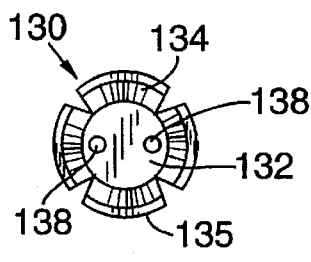

ANCHORING AND MANIPULATING TISSUE

This application is a continuation of application Ser. No. 07/715,113, filed Jun. 12, 1991 now U.S. Pat. No. 5,601,557, which was a divisional of application Ser. No. 07/192,813, filed Apr. 20, 1988, now abandoned, which was a continuation-in-part of application Ser. No. 06/848,341, filed Apr. 4, 1986, now U.S. Pat. No. 4,741,330, which was a continuation of application Ser. No. 07/496,116, filed May 19, 1983, abandoned, which was a continuation-in-part of application Ser. No. 07/380,043, fled May 20, 1982, abandoned.

BACKGROUND INFORMATION

This invention relates to an apparatus and method for manipulating and anchoring cartilage and similar fibrous tissue within a joint.

Conventional medical clamps have certain disadvantages when used for manipulating cartilage or other tissue within a joint during arthroscopic surgery. Primarily, the clamps have a tendency to slip off the cartilage. Additionally, the size of the clamps in relation to the relatively small space within the joints makes it difficult to maneuver other surgical instruments, such as a scalpel or arthroscope, within the confined space of the joint. Such clamps can also interfere with the view of the inside of the joint afforded by the arthroscope. Since the clamps must be introduced into the joint through an incision, they are limited in their range of manipulation by the location of the incision. In order to apply a desired directional traction to the cartilage, it may be necessary to release the clamp from the cartilage, reintroduce the clamp through another incision, and reclamp the cartilage.

It is often necessary to repair torn fibrous tissue, such as a ligament or tendon, or reattach such tissue to bone. While in some instances it is possible to insert two needles into the joint and then thread both of them with a suture to form a loop to reattach torn parts of fibrous tissue, that procedure is undesirable because it is complex and time-consuming. The alternative of more radical arthrotomy is also undesirable because of the increased amount of trauma and resultant increased morbidity encountered in the use of such a procedure.

As is explained in the following summary and description, the present invention provides a relatively compact and easy to use apparatus for manipulating cartilage and other fibrous tissue, and for anchoring the tissue to other tissue or to bone. Some technical references that may be of general interest are as follows: Allen, U.S. Pat. No. 3,699,969; Shein, U.S. Pat. No. 3,527,223; Woo, U.S. Pat. No. 3,943,932; Almen, U.S. Pat. No. 3,500,820; Johnson et al., U.S. Pat. No. 3,871,368; and Smith, U.S. Pat. No. 4,243,037. None of these references discloses a method or apparatus suitable for manipulating fibrous tissue during arthroscopic surgery, or for effectively reattaching fibrous tissue to bone or to other fibrous tissue.

SUMMARY OF THE INVENTION

The aforementioned problems associated with use of conventional medical clamps for manipulating tissue are overcome by the present invention, which provides an apparatus and an associated method for manipulating and anchoring tissue during arthroscopic surgery. The apparatus provides adequate fixation of the tissue during such surgery and minimally interferes with the use of other instruments within the joint.

The apparatus particularly comprises an elongated anchor member having a suture attached proximate the midpoint of its length. The anchor member is inserted through the tissue with the suture extending therefrom to provide a mechanism for manipulating the tissue within the joint. The end faces of the anchor may be slanted to facilitate movement of the anchor member through the tissue.

The preferred means of inserting the anchor member includes a hollow needle having a sharp tip and an open butt. A hollow tube of equal or greater length than the needle slides within the needle. A limiting mechanism is provided at the butt of the needle and at the corresponding portion of the hollow tube to selectively position the tube within the needle so that the tube does not extend outwardly beyond the tip of the needle.

The anchor member is located within the tip of the hollow needle in either a deformed U shape, or in its normal, substantially straight shape. The suture extends from the anchor member through the bore of the tube.

A removable shield fits over the tip of the needle to prevent the sharp tip from cutting the suture or the anchor member during the process of inserting the anchor member into the hollow needle.

With the anchor member located within the tip of the needle, the needle tip is inserted into a joint during a surgical procedure. The needle tip pierces the tissue to be anchored and passes substantially through the tissue. The limiting mechanism is manipulated so that the tube may be pushed forward to the tip of the needle, thereby expelling the anchor member from the tip of the needle into or behind the piece of tissue to be anchored. As the anchor member is expelled from the tip of the needle it assumes an orientation generally perpendicular to the length of the suture. The needle and tube are then removed from the joint, leaving the suture extending through the tissue and out of the joint. The tissue is manipulated by the application of tension on the suture.

If it is desirable to push the tissue, the suture may be rethreaded or left threaded in the tube and the tissue may then be securely held between the tube and the anchor member by applying tension to the suture. If it is desirable to control the tissue from a different angle, or through a different incision, a hook-ended instrument may be passed through another incision to hook the suture and pull the tissue. It will be apparent that moving the tissue in this manner is possible without detaching the anchor member from the tissue. If necessary, the tissue may be removed from the joint by tension On the suture once the tissue has been surgically freed from the joint.

It is often desirable to permanently reattach to bone fibrous tissue, such as tendons or ligaments. An alternative embodiment of a tissue anchoring apparatus is provided for that purpose. More particularly, the apparatus of this embodiment includes a deformable anchor member that has a base and at least two legs. Each leg is attached to the base and extends therefrom to terminate in an outer end. A suture is attached to the base of the anchor member. The anchor member is formed of resilient material for urging the anchor member into a relaxed position wherein the ends of the legs are spaced apart a maximum distance. The anchor member is deformable into a deformed position wherein the ends of the legs are spaced apart a minimum distance that is less than the maximum distance.

While in the deformed position, the anchor member is insertable into a hole that is drilled into the bone at the location the tissue is to be attached to the bone. The hole has a diameter that is less than the maximum distance between the ends of the anchor member legs. Consequently, upon insertion of the anchor member into the hole, the ends of the anchor member legs bear upon the bone within the hole, and the suture extends from the hole. Whenever tension is applied to the suture, the ends of the legs dig into the bone and resist removal of the anchor member from the hole.

With the anchor member anchored in the hole, the suture is available for securing the tissue to the bone. One way of using the suture to secure the tissue to the bone is to attach a retainer to the suture for pressing the tissue against the bone. The retainer includes resilient suture-engaging edges and corners, and is slidable along the suture in one direction, but grips the suture to resist sliding in the opposite direction. The retainer thereby holds tissue against the bone during healing so that the tissue will properly reattach to the bone.

To avoid prolonged irritation of surrounding tissues, the anchor member, suture, and retainer of the present invention may be made of material that is gradually absorbable by the body.

The foregoing and other features of the invention will be more readily understood upon consideration of the following detailed description of the invention, taken in conjunction with the accompanying drawings.

BRIEF DESCRIPTION OF THE DRAWINGS

FIG. 1 is an elevational view of an apparatus for manipulating and anchoring tissue according to the present invention, with a portion of the apparatus sectionally cut away.

FIG. 2 is a sectional elevational view of the apparatus shown in FIG. 1, illustrating the manner of deformably lodging an anchor member within the tip of a hollow needle.

FIG. 3 is a fragmentary, sectional elevational view of the apparatus of FIG. 1, showing the apparatus piercing cartilage.

FIG. 4 is a fragmentary, sectional elevational view of the apparatus of FIG. 1, illustrating the manner of expelling the anchor member between cartilage and bone.

FIG. 5 is a sectional elevational view of the apparatus of FIG. 1, showing cartilage secured by the anchor member and suture components of the apparatus.

FIG. 6 is an enlarged perspective view of the anchor member and suture, showing the normal and deformed configuration of the anchor member.

FIG. 7 is a foreshortened perspective view of a hook-ended instrument usable with the apparatus of FIG. 1.

FIG. 8 is a sectional elevational view of an apparatus for manipulating and anchoring tissue, illustrating an alternative manner of lodging the anchor member within the tip of the needle.

FIG. 9 is a sectional elevational view of the apparatus shown in FIG. 8, illustrating expulsion of the anchor member from the tip of the needle.

FIG. 10 is a perspective view of the inner surface and an edge of a retainer used in association with the suture and the anchor member for securing tissue to bone or to other tissue.

FIG. 11 is a perspective view of the outer surface and an edge of the retainer shown in FIG. 10.

FIG. 12 is a perspective view of an alternative retainer.

FIG. 13 illustrates a portion of a joint in which the anchor member, suture, and retainer are used to connect and retain a piece of cartilage in position against another piece of cartilage from which it had been torn.

FIG. 14 is a sectional view taken along line 14—14 of FIG. 13.

FIG. 15 is a side elevational view, partly in section, of an anchor member and suture that can be anchored to a bone.

FIG. 16 is a sectional elevational view of the anchor member and suture of FIG. 15, positioned within the preferred mechanism for inserting the anchor member into a hole in a bone.

FIG. 17 is a sectional elevational view showing the anchor member of FIG. 16 anchored within a hole in a bone and used, in conjunction with the suture and a retainer, to hold tissue against the bone.

FIG. 18 is a sectional elevational view showing an alternative method of using an anchor member and suture to hold tissue against the bone.

FIG. 19 is a side cross-sectional view of an alternative embodiment of an anchor member that has a hole formed therethrough to permit a suture to be looped through it.

FIG. 26 is a cross-sectional view of another alternative embodiment of an anchor member than can be anchored to a bone.

FIG. 21 is a top view of the anchor member of FIG. 20.

DESCRIPTION OF PREFERRED EMBODIMENTS

One preferred embodiment of the present invention, shown assembled in FIGS. 1 and 2, provides a resiliently deformable anchor member 10, which is attached to a suture 12 and adapted to fit deformably within the tip 26 of a hollow needle 14. A hollow tube 16, also adapted to fit within the needle 14, is used to expel the anchor member from the tip 26 of the needle after the needle has pierced a piece of fibrous tissue, such as the cartilage 18, as shown in FIGS. 3 and 4. Once expelled between the cartilage 18 and bone 38, the anchor member resiliently resumes its normal shape, as shown in FIG. 5. The anchor member of the invention might also be used to secure ligament or tendon, as will be described hereinafter, and the term tissue will be broadly used herein to encompass cartilage, tendons, ligaments and similar tissue.

The anchor member 10, shown in perspective view of FIG. 6, is an elongated cylindrical member. The anchor member 10 has end faces 20 and 22 at the respective extremities thereof. The end faces 20 and 22 are slanted relative to the longitudinal axis of the anchor member and preferably lie in respective planes that intersect one another. The suture 12 is attached to the anchor member 10 at a location 24 between the end faces 20 and 22. The suture 12 may be attached to the anchor member 10 during formation of the anchor member.

The anchor member 10 is preferably comprised of a resilient material such as a plastic. As a result, the anchor member is capable of being deformed from its relaxed, straight shape into a U-shape as shown in broken line in FIG. 6. Although the anchor member is shown to have a circular cross section, other cross-sectional shapes could be utilized without departing from the principles of this invention.

The anchor member 10 is formed with sufficient rigidity to cause it to resist deformation under moderate pressure, but not so rigid as to prohibit the U-shaped deformation when the anchor member is lodged within the needle as shown in FIG. 2 and 3. The material comprising the anchor member has sufficient elasticity to restore the anchor member substantially to its relaxed, straight configuration shown in FIGS. 1, 4, 5 and 6.

The needle 14 shown in FIGS. 1 and 2 has a hollow cylindrical shape with a sharp-edged open tip 26, an open butt 27, and a bore extending longitudinally therethrough from the tip 26 to the butt 27. The sharp tip 26 is beveled to create a sharp edge at its outer circumference and is thereby adapted to pierce and penetrate tissue. Alternatively, the sharp tip 26 could be beveled to create a sharp edge at its inner circumference.

An annular collar 28, which includes an open keyway 30 formed therein, encircles the butt of the needle. The keyway extends a short distance toward the needle tip through the cylindrical wall of the needle as shown in FIG. 2.

The hollow tube 16, which is at least as long as the needle 14, and has an elongated cylindrical shape with an open tip 17 and an open butt 19, is adapted to slide within the hollow needle. The tube 16 has an interior bore diameter large enough to receive the suture 12 therethrough so that the free end 13 of the suture extends from the open butt 19 of the tube. The tube 16 has an annular flange 32 encircling the butt 19 thereof to prevent the tube, when pushed toward the needle tip 26, from protruding more than a predetermined distance beyond the tip. The tube is preferably such a length that when the flange 32 is positioned immediately adjacent the collar 28, the tip 17 of the tube is proximate the needle tip 26, as shown in FIG. 4.

A limiting mechanism for controlling movement of the tube 16 is provided in the form of a key 34 that is mounted on the outer cylindrical wall of the tube 16. The key 34 is adapted to mate with the keyway 30 associated with the needle 14. The key 34 will prevent the tip 17 of the tube 16 from moving proximal to the tip 26 of the needle 14 unless the key 34 is aligned with the keyway 30. This alignment is accomplished by rotation of the tube 16 within the needle 14. If the tube 16 is of the aforementioned preferred length, the key 34 should be located close enough to the tip 17 of the tube 16 to permit the anchor member 10 to be fully drawn into the needle tip 26 when the tube is positioned inside the needle with the key and keyway out of alignment, as shown in FIGS. 2 and 3. As will be apparent, the keyway 30 should be of sufficient length to allow the flange 32 to contact the collar 28 when the key 34 is positioned in the keyway 30. It should be recognized that, while a aforedescribed key and keyway arrangement is believed to be particularly suitable, other mechanisms for limiting the movement of the tube 16 within the needle 14 could be utilized without departing from the principles of this invention.

As shown in FIGS. 1 and 2, a shield 36 having a generally cylindrical shape with open ends is adapted to fit removably on the sharp needle tip 26. The inner walls of the shield have three distinct sections: an upper section 29, an intermediate section 31, and a lower section 33. The upper section 29 is cylindrical and has an inner diameter substantially equal to the outer diameter of the needle tip 26 so as to permit the shield to be mounted over the tip 26. The intermediate section 31 is cylindrical and has an inner diameter slightly smaller than the outer diameter of the needle tip 26, to shield the anchor member from the sharp edge of the needle tip 26. The lower section 33 has a bell-like flared shape to encourage appropriate deformation of the anchor member 10 as it is drawn into the needle tip 26 as shown in FIG. 2.

Prior to use, the apparatus is first assembled as shown in FIGS. 1 and 2, the shield 36 being mounted upon the tip 26 prior to the suture 12 being threaded through the tube 16 so that the free end 13 protrudes out the butt end 19 of the tube. Tension on the free end 13 of the suture 12 will pull the anchor member 10 into the needle tip 26 as shown in FIG. 2, the inner surface of the bell-shaped lower section 33 of the shield guiding the anchor member into the appropriate U-shape, the anchor member being protected from the sharp tip by the shield 36.

The tube 16 is axially positioned within the needle with the key 34 abutting the collar 28 so that there is appropriate space for the anchor member to lodge deformably within the needle tip 26. Positioning the tube 16 within the needle as shown in FIGS. 1 and 2 is not necessary prior to introducing the free end 13 of the suture 12 into and through the bore of the needle 14, but having the tube so positioned when the anchor member 10 is drawn into the tip 26 is helpful to ensure that the anchor member 10 is not positioned an unnecessary distance from the needle tip 26. Once the anchor member 10 is deformably lodged in the tip 26, the shield 36 may be removed.

The assembled apparatus may then be introduced into the joint of a patient, either through an incision or by using the needle tip 26 to pierce the skin and surrounding tissue. The tip 26 of the needle 14 is thereafter used to pierce the cartilage 18 which is to be manipulated or anchored, as shown in FIG. 3.

One the tip 26 has pierced the cartilage 18, the tube 16 may be axially rotated within the needle 14 so that the key 34 aligns with the keyway 30. The tube 16 may then be pushed toward the tip 26 of the needle 14, the key 34 entering the keyway 30, and the tip 17 of the tube 16 expelling the anchor member 10 from the needle tip 26 as shown in FIG. 4. As the anchor member 10 is pushed from the needle tip 26, it resumes its normal elongated shape. Where the cartilage 18 is very near bone 38, the slanted end faces 20, 22 of the anchor member facilitate movement of the longitudinal extremities of the anchor member through the space 40 between the bone 38 and cartilage 18.

Once the anchor member 10 has generally resumed its normal elongated shape behind the cartilage 18, the needle 14 and the tube 16 may be withdrawn from the joint, allowing the cartilage 18 to partially collapse around the anchor member 10 and suture 12 as shown in FIG. 5. The suture 12 is now anchored to the cartilage 18, and the cartilage may be securely held and manipulated by tension on the suture 12 to facilitate further surgical procedures on and around the cartilage.

The relatively small size of the suture 12 allows virtually unobstructed vision of the interior of the joint through an arthroscope, and also permits the insertion of other surgical instruments, such as an arthroscope or scalpel, through the same incision as the suture. Due to the flexibility of the suture 12, tension may be applied from many directions as dictated by the needs of the surgical process. Further control of the cartilage 18 is available by rethreading the suture 12 through the tube 16 and applying tension to the suture, thereby effectively clamping the cartilage 18 between the anchor member 10 and the tip 17 of the tube 16, and allowing the cartilage to be pushed, rather than pulled, into a desired position.

A hook-ended instrument 42, shown in FIG. 7, may be used to achieve even greater maneuverability of the anchored cartilage 18 by introducing the instrument 42 into the joint through a separate incision, capturing the suture 12 in the hooked end of the instrument, and drawing the suture 12 out of the joint through such other incision. The cartilage may then be manipulated and controlled in the manner described above, through a different incision, without detaching the anchor member 10 from the anchor cartilage 18.

If necessary, the anchored cartilage 18 may be surgically freed, and removed from the joint by tension on the suture 12.

Referring now to FIGS. 8 and 9, an anchor member 50, which is similar to the anchor member 10 described above, has fixedly attached thereto a suture 52. The anchor member 50 is held within the tip 53 of a hollow needle 54, ahead of the tip 56 of a hollow tube 55. The edge of the hollow needle 54 at the tip 53 is formed in a plane that is slanted relative to the longitudinal axis of the needle, thereby to form a sharp leading edge 51 for piercing tissue. The free end 57 of the suture 52 extends from the hollow tube 55.

As shown in FIGS. 8 and 9, the anchor member 50 may be used in essentially the same fashion as is the anchor member 10, with the hollow needle 54 piercing a piece of fibrous tissue, such as cartilage 60. The anchor member 50 is expelled from the tip 53 of the hollow needle 54 as the hollow tube 55 is slid toward the tip 53 of the hollow needle 54. The anchor member 50 thereafter assumes a position between the cartilage 60 and a bone 62, where it extends generally perpendicular to the suture 52. The slanted end faces 64, 65 of the anchor member 50 assist in directing the anchor member 50 to this position. Once the anchor member 50 has been expelled from the needle 54, the suture 52 is pulled outwardly to move the anchor member 50 to the position shown in broken line in FIG. 9, where it extends laterally along the lower surface of the cartilage 60.

It is noteworthy that the anchor member 50 depicted in FIGS. 8 and 9 may be formed of substantially rigid material. A rigid anchor member can be inserted into the space between the cartilage and bone by moving the needle 54 so that it is inclined to the bone surface and then expelling the anchor member from the needle.

A rigid anchor member may be lodged within cartilage or other tissue (i.e., as opposed to being inserted between cartilage and bone) by expelling the anchor member substantially straight into the tissue and pulling on the suture. Because the suture is attached between the ends of the anchor member, tension on the suture tends to rotate the anchor member into a position substantially perpendicular to the suture, thereby causing the anchor member to become firmly lodged within the tissue. In this regard, rotational movement of the anchor member 50 into a position substantially perpendicular to the suture 52 most readily occurs when the end face 65 that last enters the tissue is slanted so that a force applied perpendicular to that surface (that force being a component of the reaction force of the tissue against the surface 65 as tension is applied to the suture of the expelled anchor member) tends to move that face 65 of the anchor member 50 away from the suture 52. This preferred slanting of the end face 65 is shown in FIGS. 8 and 9.

Referring now to FIGS. 10–14, retainer devices 68 and 69, each having a pair of generally parallel surfaces, are made of resilient material and have slits 70 and 72, respectively, which intersect near the central points of the parallel surfaces, defining pointed corner flaps 71 and 73, respectively. The retainers 68 and 69 are preferably circular because the circular shape may reduce the possibility of irritation of surrounding tissue. It will be understood, however, that this shape is a matter of choice and that other shapes would also be acceptable.

Raised points 74 are provided on the inner surface of the retainer 68 to bear against tissue, and to assist in immobilizing the tissue while the anchor member is in use. In many instances, however, the raised points 74 will not be required and a flat inner surface will suffice. The following discussion of retainer use is directed to the anchor member 50 of FIG. 8; however, it is understood that the discussion applies to all embodiments of the anchor member described herein.

The retainer 68 (or retainer 69) may be used in conjunction with the anchor member 50 by inserting the free end 57 of the suture through the retainer at the intersection of the slits 70 after the hollow needle and hollow tube have been withdrawn from around the suture. When the suture 52 is inserted through the retainer 68, the flaps 71 that are defined between adjacent slits 70 are resiliently deformed toward the direction of movement of the suture therethrough. Thereafter, the flaps wedge against the suture 52 and resist withdrawal of the suture through the slits. By applying tension to the suture 52 (see FIGS. 13 and 14) and urging the retainer 68 along the suture to the surface of cartilage 76 from which the suture extends, the retainer may be used to maintain tension in the suture, thereby holding a loose piece of cartilage 76 against the stable piece of cartilage 78 from which the loose piece of cartilage 76 had been torn or fractured.

The anchor member 50, suture 52, and retainer 68 may be left permanently in the joint to retain the torn cartilage 76 in its proper location against the stable cartilage 78, with the retainer 68 resting against the outside of the stable cartilage 78, between the surface of the stable cartilage 78 and muscle tissue 79 adjacent thereto.

It is noteworthy that in many instances the needle 54 may be inserted into a joint from opposing directions. For example, the anchor member 50 was deposited in the position shown in FIGS. 13 and 14 by a needle that penetrated the muscle tissue 79. The needle could have been inserted from the opposing side of the joint (and not through the muscle tissue 79) to deposit the anchor member 50 in the position occupied by the retainer 68 in FIGS. 13 and 14. Accordingly, the positions of the anchor member 50 and the retainer 68 would be reversed from those shown in FIGS. 13 and 14, but the loose cartilage 76 would still be held against the secure cartilage 78. One reason for inserting the needle from the opposing side of the joint, as just explained, would be to avoid damaging any nerves or blood vessels that are present in the region of the muscle tissue 79.

To prevent prolonged irritation of the surrounding tissue by the presence of the anchor member 50 and retainer 68, it is particularly desirable to form the anchor member and retainer of material that can be gradually absorbed by the body of the patients as healing occurs. Resilient, synthetic materials that are gradually absorbable by the body are known for use in sutures and are desirable as materials for the anchor member and retainers of the present invention. One such material is an absorbable polymer known as polydiaxonone (PDS), which is available from Ethicon, Inc., of Summerville, N.J.

Referring now to FIGS. 15–17, an anchor member 80 is particularly adapted for use in anchoring a suture 82 to bond 96 so that the suture 82 may be used to reattach tissue 98 to the bone. The anchor member 80 is generally bullet-shaped having a rounded convex base 84 with two attached legs 86 extending from the base. The outer ends 85 of the legs are tapered and terminate in a sharp outer edges 87. The anchor member 80 is formed of resilient material, and whenever the anchor member is in its relaxed state (FIG. 15), the legs 86 diverge outwardly so that the outer edges 87 of the legs are spaced apart a maximum distance D. One end of a suture 82 is embedded within, or otherwise attached to, the base 84 of the anchor member 80. Suture 82 extends outwardly from the base 84 between the legs 86.

Preferably, the outer surface of the anchor member 80 carries a plurality of barbs 88. The barbs 88 point outwardly, and away from the rounded convex base 84. As a result, the exposed sharp point of each barb 88 is directed generally toward the direction in which the suture 82 extends away from the base 84 of the anchor member 80.

As shown in FIG. 16, the anchor member 80 is inserted within the tip 93 of a hollow needle 90 ahead of the tip 91 of a tube 92 that is used to expel the anchor member 80 from the needle. The suture 82 extends through the bore of the tube 92.

The anchor member 80 and the bore of the needle 90 are sized so that the anchor member is in a deformed position whenever it is lodged within the tip 93 of the needle. In the deformed position, the legs 86 of the anchor member are pressed together with the outer edges 87 of the legs being spaced apart a minimum distance D corresponding to the needle bore diameter. This distance D is less than the maximum distance D between the outer edges 87 as measured when the anchor member is in the relaxed position (FIG. 15).

As noted, the anchor member 80 is formed of resilient material. Consequently, whenever the anchor member 80 is expelled from the needle 90, the intrinsic resilience of the anchor member urges it into the relaxed position. As will now be explained, the tendency of the anchor member 80 to move from the deformed into the relaxed position provides a simple mechanism for anchoring the anchor member 80 in bone so that, in conjunction with the attached suture; there is provided a means for reattaching tissue to the bone to promote healing.

More particularly, with reference to FIG. 17, a hole 100 is drilled into the bone 96 in the region where the tissue 98 is to be reattached to the bone. The hole diameter is less than the maximum distance D between the outer edges 87 of the anchor member, but greater than or equal to the bore diameter of the needle 90. With the anchor member 80 within the tip 93 of the needle 90, the tissue 98 is pierced by the needle in a manner as described earlier. The tip 93 of the needle is forced through the tissue 98 and then aligned with the hole 100. Next, the anchor member 80 is expelled from the needle into the hole 100 by sliding the tube 92 toward the tip 93 of the needle 90 as described earlier with respect to FIGS. 3–5.

Once expelled from the needle 90 into the hole 100, the resilience of the anchor member 80 urges the outer edges 87 of the legs 86 to bear upon the bone within the hole 100. With the outer edges 87 of the legs bearing upon the bone, any tension applied to the suture 82 causes the sharp edges 87 to dig into the bone to secure the anchor member within the hole. The barbs 88 also dig into the bone to supplement the anchoring effect of the legs 86.

Preferably, the anchor member 80 is sized so that when it is positioned within the hole 100, the outer edges 87 of the legs 86 are beneath a relatively dense bone layer 97 that is located at the surface of the bone 96, and is known as the cortical layer 97. As a result, tension in the suture (in conjunction with the intrinsic resilient force of the anchor member 80 that forces the leg edges 87 apart) tends to lodge the edges 87 of the anchor member legs beneath the cortical layer 97, rendering the anchor member substantially irremovable from the hole 100.

As shown in FIG. 17, a retainer 68, as described earlier, may be employed with the suture 82 to secure the tissue 98 to the bone 96.

FIG. 18 illustrates another technique for securing tissue 99 to the bone 96, wherein two anchor members 80 are anchored in holes 101, 103, and the free ends of the sutures 82 are tied together over the tissue.

It is noted that it may not be necessary to first pierce the tissue 99 before depositing the anchor member 80 into the hole 101, 103. For instance, the anchor member 80 may be deposited within the hole 101, 103 in the manner described above, and the free end of the suture 82 may be threaded through a conventional surgical needle that is used to pierce the tissue. The surgical needle is then removed and the free ends of the sutures 82 are secured as described above.

FIG. 19 depicts an alternative embodiment of an anchor member 110 suitable for anchoring in bone. The anchor member 110 is substantially similar to the anchor member 80 described earlier, except that it includes a continuous passage 112 formed therein to pass into one leg 114, through the base 116, and out the other leg 115. The suture 118 is threaded through the hole passage 112 so that two suture segments 120 extend from the anchor member. This configuration of the anchor member 110 allows the user to select any type of suture for use with the anchor member 110, depending upon the particular surgical needs. Further, having two suture segments 120 available for securing the tissue to the bone is often desirable. For example, whenever an odd number of anchor members 116 is used, the resulting even number of available suture segments 120 permits each segment of one anchor member to be tied to a corresponding segment of an adjacent anchor member, without the need for tying more than two suture segments together.

FIGS. 20 and 21 illustrate a side sectional view and top view, respectively, of another alternative embodiment of an anchor member 130 formed in accordance with this invention. This embodiment is a generally cup-shaped piece of resilient material, such as plastic, having a base 132 with four legs 134 extending upwardly therefrom. The sharp outer edge 136 of each leg is spaced apart from an opposing edge 136 by a maximum distance D whenever the anchor member is in the relaxed position as shown in FIG. 20. As noted earlier, distance D is greater than the diameter of the hole into which the anchor member 130 is deposited. Preferably, two holes 138 are formed in the base 132 of the anchor member 130. A suture 140 is threaded through the holes 138.

The anchor member 130 is deposited within a hole in a bone in a manner similar to that explained with respect to the apparatus of FIG. 16. Specifically, the anchor member 130 is positioned within the tip of a hollow needle (not shown) where it assumes a deformed position. In the deformed position, the outer edge 136 of each leg is held near the outer edge 136 of the opposing leg a distance D that is less than the "relaxed" distance D and corresponds to the diameter of the needle bore in which the anchor member is lodged. When the anchor member 130 is expelled from the needle and deposited within the hole in the bone, the intrinsic resilience of the anchor member 130 forces the outer edges 136 against the bone, thereby anchoring the anchor member within the hole. The suture 140 is thereafter available to secure tissue against the bone as discussed above.

The anchor members 80, 110, 130 just described may be formed of material that is absorbable by the body. Alternatively, the anchor members may be formed of non-absorbable material (e.g., stainless steel of suitable resilience) that remains in the bone indefinitely.

The terms and expressions that have been employed in the foregoing specification are used herein as terms of description and not of limitation, and there is no intention, in the use of such terms and expressions, of excluding equivalents of the features shown and described or portions thereof, it being recognized that the scope of the invention is defined and limited only by the claims that follow.

I claim:

1. A method for anchoring in bone a member and attached suture, comprising the steps of:

forming a hole in the bone;

attaching a suture to a member; and lodging the member within the hole solely by pressing the member with attached suture into the hole so that the member becomes lodged therein in the absence of any manipulation of the member other than pressing the member with attached suture into the hole.

2. The method of claim 1 wherein the forming step includes the step of making the depth of the hole deeper than the cortical layer of the bone and wherein the lodging step includes the step of locating the member beneath the cortical layer.

3. The method of claim 1 including after the lodging step, the step of attaching tissue to the suture so that the tissue is secured against the bone.

4. The method of claim 1, including prior to the attaching step, the step of constructing the member to be a resilient, unitary member.

5. A method for anchoring a member in a bone, comprising the steps of threading a suture through the member;

forming a hole in the bone; and pressing the member into the hole so that two contiguous segments of the suture extend from the hole.

6. The method of claim 3 wherein the tissue is a member of the group consisting of cartilage, tendon, or ligament.

7. The method of claim 5 including the step of selecting the member to be deformable and of a size such that the member is lodged within the hole solely as a result of the pressing step.

* * * * *